United States Patent [19]

Jacob et al.

[11] Patent Number: 4,957,926
[45] Date of Patent: Sep. 18, 1990

[54] METHOD OF TREATING HERPESVIRUSES

[75] Inventors: Gary S. Jacob, Oxford; A. Stanley Tyms, London; Thomas W. Rademacher; Raymond A. Dwek, both of Oxford, all of United Kingdom

[73] Assignee: Monsanto Company, St. Louis, Mo.

[21] Appl. No.: 288,528

[22] Filed: Dec. 22, 1988

[51] Int. Cl.$^5$ ............................................ A61K 31/445
[52] U.S. Cl. ..................................................... 514/315
[58] Field of Search ........................................ 424/315

[56] References Cited

U.S. PATENT DOCUMENTS 4,182,767  1/1980  Murai et al. ......................... 424/267
4,639,436  1/1987  Junge et al. ............................ 514/24

FOREIGN PATENT DOCUMENTS

WO87/03903  7/1987  PCT Int'l Appl. .

OTHER PUBLICATIONS

Nieman et al, Gesell. Biolog. Chemie 365, 1040, Abs. A59 (1984).
Repp et al, The Journal of Biol. Chemistry, vol. 260, No. 29, 15873–15879 (1985).
Fleet et al., FEBS Lett. 237, 128–132 (1988).
Karpas et al., Proc. Natl. Acad. Sci. USA 85, 9229–9233 (1988).
Datema et al., Pharmac. Ther. 33, 262–269 (1987).
Tyms et al., The Lancet, Oct. 31, 1987, pp. 1025–1026.

Primary Examiner—Jerome D. Goldberg
Attorney, Agent, or Firm—Scott J. Meyer; James W. Williams, Jr.

[57] ABSTRACT

A method is disclosed for the treatment of herpesvirus infections comprising treating the infected host with an effective amount of an N-alkyl derivative of deoxynojirimycin in which the alkyl group contains from one to about six carbon atoms, and preferably is butyl.

9 Claims, 1 Drawing Sheet

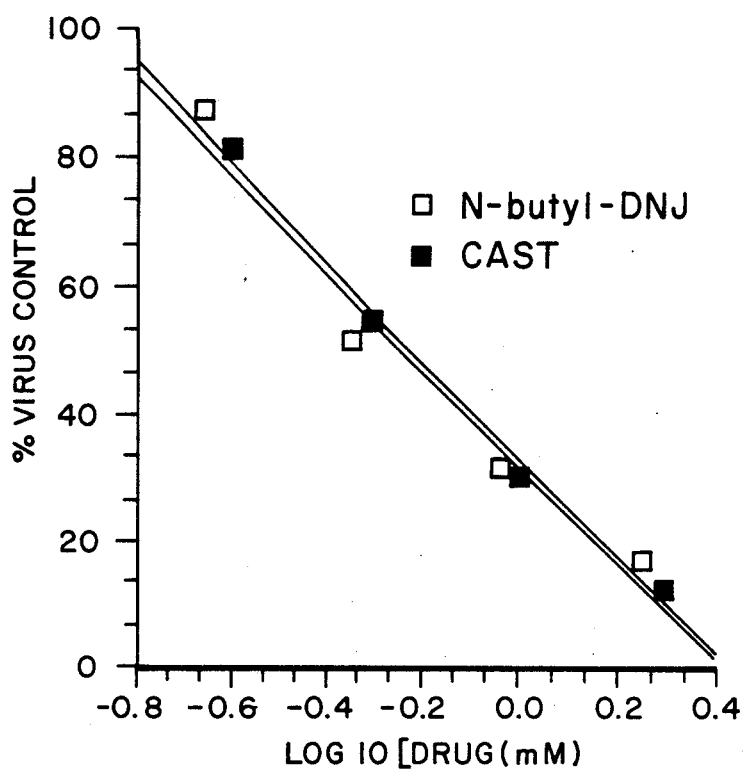

METHOD OF TREATING HERPESVIRUSES

BACKGROUND OF THE INVENTION

This invention relates to a method for the treatment of herpesviruses and, more particularly, to the use of N-alkyl derivatives of 1,5-dideoxy-1,5-imino-D-glucitol for inhibiting viruses of the Herpesviridae family, e.g., herpes simplex virus (HSV), varicella-zoster virus, cytomegalovirus (CMV) and Epstein-Barr virus (EBV).

The herpesviruses are a family of DNA viruses which have a special affinity for cells of ectodermal origin and tend to promote latent infections. Herpesviruses are a major cause of disease in humans. Coincident infection by these viruses also is common in patients having acquired immune deficiency syndrome (AIDS).

Various drugs and other therapeutic treatments have been indicated for use against herpesviruses. The use of various purine, pyrimidine and pyrrolidine derivatives for this purpose, e.g., the purine and pyrimidine acyclic nucleosides, is particularly noteworthy. Two such compounds are 9-[(2-hydroxyethoxy)methyl]-guanine or acyclovir and the analogous 9-(1,3-dihydroxy-2-propoxymethyl)guanine (DHPG) or ganciclovir. The use of acyclovir as an antiviral for HSV is described, for example, by Schaeffer, *Nature* 272, 583(1978); Balfour, *Ann. Rev. Med.* 35, 279-291 (198); and in U.S. Pat. Nos. 4,199,574 and 4,758,572. Use of ganciclovir for treatment of CMV in AIDS patients, especially against CMV retinitis, is disclosed, for example, by Bach et al., *Ann. Inter. Med.* 103, 381-382 (1985); Masur et al., *Ibid.* 104, 41-44 (1986); and The Collaborative DHPG Treatment Study Group, *N. Engl. J. Med.* 314, 801-805 (1986). The in vitro activity of acyclovir against CMV infections in a plaque reduction assay is described by Tyms et al., *J. Antimicrobial Chemotherapy* 8, 65-72 (1981). The antiviral activity of ganciclovir against CMV infection in a cell culture model is described by Tyms et al., *J. Gen. Virology* 68, 1563-1573 (1987).

Another type of compound reported to be useful against herpesviruses is the glycosylation inhibitor 2-deoxy-D-glucose. The activity of this compound against HSV is described, for example, by Courtney et al., *Virology* 52, 447-455 (1973); Blough, *J. Amer. Med. Assn.* 241(26), 2798-2801 (1979); Blough et al., *Biochem. Biophys. Res. Commun.* 141(1), 33-38 (1986): and in U.S. Pat. No. 4,315,001.

Recently, certain plant alkaloid inhibitors of glucosidase activity which were found to block the growth of the AIDS-associated virus HIV were also suggested as potentially active against cytomegalovirus replication. See Tyms et al., *Lancet*, Oct. 31, 1987, pp. 1025-1026. The reported alkaloids were castanospermine (CAST), dihydroxymethyldihydroxypyrrolidine (DMDP) and 1deoxynoirimycin (DNJ). The latter compound is alternatively named 1,5-dideoxy-1,5-imino-Dglucitol.

The use of CAST, DMDP, DNJ and the N-methyl derivative of DNJ against AIDS-associated retroviruses is further disclosed in PCT Inter. Appln. WO 87/03903, published July 2, 1987.

The use of the N-butyl derivative of DNJ for inhibition of human immunodeficiency virus (HIV) is disclosed by Fleet et al., *FEBS Lett.* 237, 128-132 (1988) and in copending applications Ser. No. 166,065, filed Mar. 9, 1988 and Ser. No. 248,461, filed Sept. 23, 1988. Its synthesis and use for various other therapeutic indications is described in U.S. Pat. Nos.4,182,767 and 4,639,436. The latter patent also discloses methods for making other N-alkyl derivatives of DNJ, e.g., the N-methyl and N-hexyl derivatives.

Further background information concerning the effects on virus multiplication by inhibitors of glycosylation can be had by reference to the recent review article by Datema et al., *Pharmac. Ther.* 33, 221-286 (1987). The use of oligosaccharide processing inhibitors CAST, DNJ, and similar agents against DNA viruses such as HSV CMV, EBV and varicella-zoster virus is described at pages 262-269.

BRIEF DESCRIPTION OF THE INVENTION

In accordance with the present invention, the N-alkyl derivatives of 1,5-dideoxy-1,5-imino-Dglucitol (N-Alk-DNJ), in which the alkyl group contains from one to about six carbon atoms, are used for the treatment of herpesvirus infections. In particular, the preferred N-butyl derivative of 1,5-dideoxy-1,5-imino-D-glucitol (N-Bu-DNJ) has been found to have outstanding activity against viruses of the Herpesviridae family. Its inhibitory activity against herpesviruses is illustrated herein against HSV type II and against CMV. These are DNA viruses which are distinct from retroviruses such as HIV.

DETAILED DESCRIPTION OF THE INVENTION

While the specification concludes with claims which particularly point out and distinctly claim the subject matter regarded as forming the present invention, it is believed that the invention will be better understood from the following detailed description of preferred embodiments of the invention taken in conjunction with the accompanying drawings in which:

FIG. 1 is a graphical representation showing plaque reduction assay results in which the % virus control is plotted against the concentration of test compounds (drug) shown as the Log 10 [drug (mM)]. The virus in this embodiment of the invention is CMV and the test compounds are N-butyl-DNJ and castanospermine.

In general, the in vitro antiviral activity of test compounds against herpesviruses can be determined by addition of the test compound to tissue cultures infected with the respective virus. Thus, due to the lack of suitable animal models for human CMV, the viral replication during treatment with a test compound can be assayed in vitro by standard plaque assays such as described, for example, by Albrecht and Weller, *Am. J. Clin. Path.* 73, 688-651 (1980). The % inhibition of virus plaque formation by a test inhibitor (e.g. acyclovir) of HSV is further illustrated in U.S. Pat. No.758,572, and a typical plaque reduction assay for detecting antiviral activity against CMV is illustrated in U.S. Pat. No. 4,743,562.

In the present case, the antiviral activity of the preferred N-Bu-DNJ against herpesviruses is demonstrated by the plaque reduction assay described by Tyms et al., *J. Antimicrobial Chemotherapy* 8, 65-72 (1981), the disclosure of which is incorporated herein by reference. For testing the N-Bu-DNJ against HSV, the HSV Type II strain HG52 described by Timbury, *J. Gen. Virol.* 13, 373-376 (1971), and Davis et al., *Analyst* 110, 605-609 (1985), is useful. For testing against CMV, the prototype CMV AD169 strain described, for example, by Tyms et al., *J. Gen. Virol.* 68, 1563-1573 (1987), and in U.S. Pat. No. 4,743,560, is useful. Another useful CMV strain is the Towne strain described by Glazer et al., *Ann. Inter. Med.* 91, 676-683 (1979).

The N-Bu-DNJ exhibits strong antiviral activity against herpesvirus strains that produce multinucleated giant cells in vitro cell culture. The formation of multinucleated giant cells (syncytia), which result from the fusion of T4 cells with each other, is one of the most striking properties of HIV [Walker et al., *Proc. Natl. Acad. Sci. USA* 84, 8120-8124 (1987); Gruters et al., *Nature* 330, 74-77 (1987)]. Some, but not all, HSV strains also produce these multinucleated giant cells in vitro cell culture. Although the inventors are not to be bound by theory, it is believed that the antiviral activity of N-Bu-DNJ against herpesvirus strains may relate to the tendency to form such cells since N-Bu-DNJ exhibits strong antiviral activity against a HSV type II strain which forms these giant cells; whereas, in preliminary tests with a HSV type I strain which did not form such cells the N-Bu-DNJ exhibited only minor effect.

The following examples will further illustrate the invention in greater detail although it will be understood that the invention is not limited to these specific examples.

EXAMPLE I

Methods

Cells and Viruses

Human embryo fibroblast cells (HEF) were grown in Eagles minimal essential medium supplemented with 7% fetal calf serum (FCS), 9 mM sodium bicarbonate and 7 mM HEPES buffer. In maintenance medium the supplements were adjusted to 2% FCS, 13 mM sodium bicarbonate and 14 mM HEPES. CMV, strain Towne, and HSV type II, strain H652, were used in the following tests. CMV virus stocks were prepared and stored by technique as previously described by Tyms & Williamson, *Nature* 297, 690-691 (1979). Herpes virus stocks were prepared and stored by technique as previously described by Davis et al., *Analyst* 110, 605-609 (1985). The HEF were human embryonic lung fibroblasts, strain MRC-5, as described by Tyms and Williamson, *Nature* 297, 690-691 (1982).

Plaque Reduction Assays

For plaque reduction assays, 24-well culture trays were seeded with HEF cells. Confluent monolayers were infected with virus to give initially about 100 plaque-forming-units (p.f.u.) per well. After a one hour absorption period the inocula were replaced by 1.5ml of a maintenance medium incorporating 0.5% low gelling temperature agarose, supplemented with various concentrations of test compound. For tests with CMV, infected monolayers were fixed with 5% formalin in phosphate buffered saline (PBS) at 6-8 days post-infection and stained with 0.3% methylene blue after removal of the overlay; whereas, tests with HSV were conducted in the same manner but with the monolayer fixing at 2 days post infection. The mean plaque number was calculated from a multiple series of counts (e.g., duplicate, triplicate or quadruplicate), converted to a percentage of untreated controls and values plotted against the $\log_{10}$ drug concentration. The 50% effective dose (ED50) was determined from best line fits for the curves.

The results for inhibitory activity against HSV type II by N-Bu-DNJ and comparative test compounds (drug) are set forth in Tables I, II and III, below. The results for inhibitory activity against CMV are set forth in Table IV, below, and the accompanying FIG. 1.

TABLE I

Herpes Simplex Type II Plaque Reduction Assay (Viral Strain HG52; HEF Cells Strain MRC-5)

| Drug | Conc. (mM) | Plaque Count | Avg | % Virus Control |
|---|---|---|---|---|
| none | — | 73,78,93,67 | mean 78 | — |
| N-Bu-DNJ | 0.22 | 80,52 | 66 | 85 |
| N-Bu-DNJ | 0.45 | 42,53 | 47 | 60 |
| N-Bu-DNJ | 0.9 | 36,22 | 29 | 37 |
| N-Bu-DNJ | 1.8 | 41,20 | 31 | 40 |
| N-Bu-DNJ | 3.6 | 5,7 | 6 | 7.7 |
| N-Me-DNJ | 0.28 | 72,95 | 84 | 100+ |
| N-Me-DNJ | 0.56 | 79,74 | 77 | 99 |
| N-Me-DNJ | 1.12 | 63,74 | 69 | 88 |
| N-Me-DNJ | 2.24 | 48,29 | 39 | 50 |
| N-Me-DNJ | 4.48 | 9,19 | 14 | 18 |

N-Bu-DNJ = N-butyl deoxynojirimycin
N-Me-DNJ = N-methyl deoxynojirimycin

TABLE II

Herpes Simplex Type II Plaque Reduction Assay (Viral Strain HG52; HEF Cells Strain MRC-5)

| Drug | Conc. (mM) | Plaque Count | Avg | % Virus control |
|---|---|---|---|---|
| none | — | 77,94,97,88 | mean 90 | — |
| 2-Deoxy-D-glucose | 2.5 | 94,88 | 91 | 100+ |
| 2-Deoxy-D-glucose | 5.0 | 61,76 | 69 | 77 |
| Castano-spermine | 0.25 | 46,54 | 50 | 56 |
| Castano-spermine | 0.5 | 52,44 | 48 | 53 |
| Castano-spermine | 1.0 | 21,55 | 38 | 42 |
| Castano-spermine | 2.0 | 61,28 | 45 | 50 |
| Castano-spermine | 4.0 | 33,32 | 32 | 36 |

TABLE III

Herpes Simplex Type 2 Plaque Reduction Assay (Viral Strain HG52; HEF cells Strain MRC-5)

| Drug | Conc. (mM) | Plaque Count | Avg. | % Virus Control |
|---|---|---|---|---|
| none | — | 51,47,53 | 51 | — |
| N-Bu-DNJ | 0.56 | 32,33,21 | 29 | 56.9 |
| N-Bu-DNJ | 1.12 | 34,22,19 | 26 | 51.0 |
| N-Bu-DNJ | 2.25 | 10,23,8 | 14 | 27.5 |
| N-Bu-DNJ | 4.5 | 9,11,6 | 9 | 17.6 |
| N-He-DNJ | 0.56 | 16,23,9 | 16 | 31.4 |
| N-He-DNJ | 1.12 | 7,11,5 | 8 | 15.7 |
| N-He-DNJ | 2.25 | trace* | — | — |
| N-He-DNJ | 4.5 | none* | — | — |

N-Bu-DNJ = N-butyl deoxynojirimycin
N-He-DNJ = N-hexyl deoxynojirimycin
*HEF cells grew normally at 0.56 and 1.12 mM N-He-DNJ; however, at 2.25 and 4.5 mM, the HEF cell monolayers looked thin, indicating that growth of cells was affected by the drug. At these higher concentrations, plaque count alone is misleading as the actual size of the plaques is significantly reduced compared to the size of plaques in the control test.
HEF cells grew normally at all concentrations of N-Bu-DNJ.

TABLE IV

Cytomegalovirus Plaque Reduction Assay (Viral Strain Towne; HEF Cells Strain MRC-5)

| Drug | Conc. (mM) | $\log_{10}$ conc. | Plaque Count | Avg | % Virus control |
|---|---|---|---|---|---|
| none | — | — | 174,178,136,215 | 176 | — |
| N-Bu-DNJ | 0.22 | −0.66 | 159,156,144,153 | 153 | 87 |

TABLE IV-continued

Cytomegalovirus Plaque Reduction Assay
(Viral Strain Towne; HEF Cells Strain MRC-5)

| Drug | Conc. (mM) | log$_{10}$ conc. | Plaque Count | Avg | % Virus control |
|---|---|---|---|---|---|
| N-Bu-DNJ | 0.45 | −0.35 | 98,95,80,94 | 92 | 52 |
| N-Bu-DNJ | 0.90 | −0.046 | 62,51,52,59 | 56 | 32 |
| N-Bu-DNJ | 1.8 | 0.25 | 29,36,35,21 | 30 | 17 |
| none | — | — | 120,260,222,214 | 204 | — |
| Cast | 0.25 | −0.60 | 146,191,184,144 | 166 | 81 |
| Cast | 0.50 | −0.30 | 108,112,122,111 | 113 | 55 |
| Cast | 1.0 | 0 | 54,57,72 | 61 | 30 |
| Cast | 2.0 | 0.30 | 21,24,24,30 | 25 | 12 |

N-Bu-DNJ = N-butyl deoxynojirimycin
Cast = castanospermine

Determination of 50% Effective Dosage Values (ED50) from the data of Tables I, II and III was made as follows:

The mean plaque numbers determined on HEF cells exposed to varying amount of N-Bu-DNJ, N-Me-DNJ, N-He-DNJ, 2-deoxy-D-glucose and castanospermine were converted to percentage values (plaque count in presence of drug divided by mean value of untreated controls ×100), and plotted as a function of drug concentration [drug (mM)].

The 50% effective dose (ED50)—that amount of drug needed to reduce plaque count by 50%—was calculated to give the following values:

| Drug | ED50 | Correlation Coefficient | Standard Error |
|---|---|---|---|
| N-Bu-DNJ | 1.2 mM | R = 0.89 | 0.82 |
| N-Me-DNJ | 2.8 mM | R = 0.98 | 0.25 |

It is Concluded that both N-Bu-DNJ and N-Me-DNJ substantially reduce herpesvirus type II infection of HEF cells; whereas, at a concentration of 2.5 mM no inhibitory effect was observed with 2-De-D-Glu and at higher concentrations it was shown to retard growth of cells (see Table VII, below). This represents a substantial advantage for N-Me-DNJ and N-Bu-DNJ. N-He-DNJ also showed substantial antiviral activity against HSV type II up to 1.1 mM, giving an estimated ED50 of about 0.25 mM; however, cell growth also was retarded at higher concentrations. This compound thus is preferably used at lower concentrations than the N-Bu-DNJ.

In a similar manner, the Effective Dosage Values (ED50) were determined from the curves of FIG. 1. A least squares fit of the data of FIG. 1 to an equation of the form: y=mx+b gave the following values:

| Drug | m | b |
|---|---|---|
| N-Bu-DNJ | −75.95 | 31.7 |
| Cast | −77.08 | 32.9 |

From these values, a 50% effective dose (ED50) was calculated to give the following values:

| Drug | ED50 |
|---|---|
| N-Bu-DNJ | 0.57 mM |
| Cast | 0.60 mM |

It is concluded that N-Bu-DNJ reduces CMV infection of HEF cells at about the same dosage as does castanospermine. However, the N-Bu-DNJ has a decided advantage over castanospermine since it is substantially less cytotoxic as seen from Fleet et al., FEBS Lett. 237, 128–132 (1988), at Table I, compound No. 57 vs. No. 16.

Yield Reduction Assays

Antiviral activities of N-Bu-DNJ and comparative test compounds against infections with CMV (Towne strain) were also measured by the yield reduction assay as follows:

HEF cells (MRC-5) were infected at high multiplicity of infection (about one p.f.u. per cell) and incubated with various concentrations of the test compounds for 5 and 6 days post infection. The level of infectious virus shed into the extracellular fluid was determined at 5 and 6 days by plaque assays as described above, using serial dilution of extracellular fluid to bring readings on scale.

The resulting CMV infectivity titres are set forth in Table V, below, and the CMV p.f.u. measurement is set forth in Table VI, below. In Table VI, to calculate plaque-forming units (PFU) of the maintenance medium overlayering HEF cells, the plaque count at the most sensitive dilution (from Table V) was multiplied by dilution value and then by 5 (0.2 ml sample volumes used in test) to give PFU (per ml maintenance medium). (e.g. calculation of drug control: $31 \times 10^3 \times 5 = 1.6 \times 10^5$ PFU).

TABLE V

Cytomegalovirus Infectivity Titres
(Viral Strain Towne; HEF Cells Strain MRC-5)

| Drug | Conc. (mM) | Days Growth | Plaque Count $10^1$ dil. | $10^2$ dil. | $10^3$ dil. | $10^4$ dil. |
|---|---|---|---|---|---|---|
| none | — | 5 | confluent | semi-conf. | 31 | — |
| N-Bu-DNJ | 0.5 | 5 | ~200 | 16, 18 | 1; 1 | — |
| N-Bu-DNJ | 2.0 | 5 | 27; 29 | 1:2 | N.D. | — |
| Cast | 0.5 | 5 | semi-conf. | 36; 45 | 4; 3 | — |
| Cast | 2.0 | 5 | 49; 40 | 2; 4 | N.D. | — |
| none | — | 6 | confluent | semi-conf. | 58; 89 | 6, 7 |
| N-Bu-DNJ | 0.5 | 6 | ~200 | 28; 24 | 0; 1 | — |
| N-Bu-DNJ | 2.0 | 6 | 17; 5 | 0; 1 | N.D. | — |
| Cast | 0.5 | 6 | semi-conf. | 62; 31 | 6; 4 | — |
| Cast | 2.0 | 6 | 41; 29 | 2; 1 | N.D. | — |

N.D., not determined
Underlined plaque count values were used to calculate PFU shown in Table VI.

TABLE VI

Cytomegalovirus PFU Measurement

| Drug | Conc. (mM) | Days HEF Growth | PFU | % Virus Control |
|---|---|---|---|---|
| none | — | 5 | $1.6 \times 10^5$ | — |
| N-Bu-DNJ | 0.5 | 5 | $8.5 \times 10^5$ | 5.3 |
| N-Bu-DNJ | 2.0 | 5 | $1.4 \times 10^3$ | 0.88 |
| Cast | 0.5 | 5 | $2.1 \times 10^4$ | 13 |
| Cast | 2.0 | 5 | $2.3 \times 10^3$ | 1.4 |
| none | — | 6 | $3.7 \times 10^5$ | — |
| N-Bu-DNJ | 0.5 | 6 | $1.3 \times 10^4$ | 3.5 |
| N-Bu-DNJ | 2.0 | 6 | $5.5 \times 10^2$ | 0.15 |
| Cast | 0.5 | 6 | $2.3 \times 10^4$ | 6.2 |
| Cast | 2.0 | 6 | $1.8 \times 10^3$ | 0.48 |

EXAMPLE 2

The effect of N-Bu-DNJ compared to 2-deoxy-D-glucose on the growth of HEF cells (strain MRC-5) in the absence of virus was demonstrated as follows.

Triplicate titer plates were seeded with human embryo fibroblast (HEF) cells (about $7.5 \times 10^3$ cells/well), and after 4 days of growth in the absence of presence of 2-deoxy-D-glucose and N-Bu-DNJ were counted and compared to a control without test compound. The results are set forth in Table VII.

TABLE VII

| Compound | Conc. (mM) | HEF Cell Count | | | |
|---|---|---|---|---|---|
| | | Plate 1 | Plate 2 | Plate 3 | Avg |
| Control | — | $3.9 \times 10^4$ | $2.4 \times 10^4$ | $1.9 \times 10^4$ | $2.7 \times 10^4$ |
| N-Bu-DNJ | 3.8 | $2.7 \times 10^4$ | $1.9 \times 10^4$ | $3.5 \times 10^4$ | $2.7 \times 10^4$ |
| N-Bu-DNJ | 7.5 | $4.8 \times 10^4$ | $4.1 \times 10^4$ | $3.3 \times 10^4$ | $4.0 \times 10^4$ |
| N-Bu-DNJ | 15.0 | $2.4 \times 10^4$ | $1.8 \times 10^4$ | $3.9 \times 10^4$ | $2.5 \times 10^4$ |
| 2-Deoxy-D-Glu | 3.8 | $1.9 \times 10^4$ | $2.2 \times 10^4$ | $3.5 \times 10^4$ | $2.6 \times 10^4$ |
| 2-Deoxy-D-Glu | 7.5 | $9.9 \times 10^3$ | $1.0 \times 10^4$ | $6.9 \times 10^3$ | $8.9 \times 10^3$ |
| 2-Deoxy-D-Glu | 15.0 | $1.0 \times 10^4$ | $6.3 \times 10^3$ | $1.1 \times 10^4$ | $9.0 \times 10^3$ |

It is concluded from the foregoing that N-Bu-DNJ has little or virtually no inhibitory effect on the growth of normal cells whereas, by contrast, the 2-deoxy-D-glucose substantially inhibits the growth. Thus, N-Bu-DNJ appears to have a potential advantage of low toxicity in use against normal cells.

The antiviral agents described herein can be used for administration to patients infected with the herpesviruses by conventional means, preferably in formulations with pharmaceutically acceptable diluents and carriers. These agents can be used in the free amine form or in the salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the aCtive compound. A suitable route of administration is orally in the form of capsules, tablets, syrups, elixirs and the like, although parenteral administration and topical administration also can be used. Appropriate formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, PA. Because of its low cytotoxicity, the preferred N-butyl-DNJ is potentially useful topically in concentrations at least as high as about 5 to 10 mM in pharmaceutically acceptable carriers.

Various other examples will be apparent to the person skilled in the art after reading the present disclosure without departing from the spirit and scope of the invention. It is intended that all such further examples be included within the scope of the appended claims.

What is claimed is:

1. A method for the treatment of herpesvirus infections in an infected human host comprising administering to said host an effective amount to inhibit herpesvirus of 1,5-(alkylimino)-1,5-dideoxy-D-glucitol in which the alkyl group contains from one to about six carbon atoms.

2. The method of claim 1 in which the herpesvirus is a type that forms multinucleated giant cells in vitro cell culture.

3. The method of claim 1 in which the herpesvirus is herpes simplex virus type II.

4. The method of claim 1 in which the herpesvirus is cytomegalovirus.

5. A method for the treatment of herpesvirus infections in an infected human host comprising administering to said host an effective amount to inhibit herpesvirus of 1,5-(butylimino)-1,5-dideoxy-D-glucitol.

6. The method of claim 5 in which the herpesvirus is a type that forms multinucleated giant cells in vitro cell culture.

7. The method of claim 5 in which the herpesvirus is herpes simplex virus type II.

8. The method of claim 5 in which the herpesvirus is cytomegalovirus.

9. The method of claim 5 in which the 1,5-(butylimino)-1,5-dideoxy-D-glucitol is administered topically in a concentration of about 5 to 10 mM in a pharmaceutically acceptable carrier.

* * * * *